US012788750B2

(12) United States Patent
Gunnarsson et al.

(10) Patent No.: US 12,788,750 B2
(45) **Date of Patent: *Nov. 10, 2026**

(54) ORAL FORMULATION OF A THERAPEUTIC COMPOUND

(71) Applicant: ARDELYX, INC., Waltham, MA (US)

(72) Inventors: Cecilia Gunnarsson, Mölndal (SE); Magnus Swenson, Södertälje (SE); Hanna Matic, Södertälje (SE); John Salomonsson, Södertälje (SE); Eva Karlsson, Södertälje (SE)

(73) Assignee: ARDELYX, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/462,617

(22) Filed: Jan. 28, 2026

(65) Prior Publication Data

US 2026/0158022 A1 Jun. 11, 2026

Related U.S. Application Data

(63) Continuation of application No. 18/265,173, filed as application No. PCT/US2021/062069 on Dec. 6, 2021, now Pat. No. 12,539,299.

(60) Provisional application No. 63/199,078, filed on Dec. 4, 2020.

(51) Int. Cl.
*A61K 31/4725* (2006.01)
*A61K 9/16* (2006.01)

(52) U.S. Cl.
CPC ........ *A61K 31/4725* (2013.01); *A61K 9/1617* (2013.01); *A61K 9/1652* (2013.01); *A61K 9/1694* (2013.01)

(58) Field of Classification Search
CPC ................................................ A61K 31/4725
See application file for complete search history.

(56) References Cited

U.S. PATENT DOCUMENTS

| | | | | |
|---|---|---|---|---|
| 12,539,299 | B2 * | 2/2026 | Gunnarsson | A61K 9/2054 |
| 2024/0041858 | A1 | 2/2024 | Gunnarsson et al. | |
| 2025/0255860 | A1 | 8/2025 | Gunnarsson et al. | |

FOREIGN PATENT DOCUMENTS

| | | | |
|---|---|---|---|
| WO | 2010078449 | A2 | 7/2010 |
| WO | 2014169094 | A2 | 10/2014 |
| WO | 2018129556 | A1 | 7/2018 |

(Continued)

OTHER PUBLICATIONS

Bowen, P, "Particle Size Distribution Measurement from Millimeters to Nanometers and from Rods to Platelets", Journal of Dispersion Science and Technology 23 (5), 631-662 (2002).

(Continued)

*Primary Examiner* — Carlos A Azpuru
(74) *Attorney, Agent, or Firm* — Viksnins Harris Padys Malen LLP

(57) ABSTRACT

The present invention provides a pharmaceutical tablet formulation of tenapanor that is chemically stable and soluble comprising greater than about 6% w/w of amorphous tenapanor in its bis-HCl form, an acidifying agent, an antioxidant, a disintegrant, a lubricant, a glidant, a filler, and an immediate release coating, wherein the total chloride content of the active ingredient is greater than 5.82% and the particle diameter distribution D50 is from about from about 18 μm to about 22 μm.

1 Claim, 12 Drawing Sheets

(56) References Cited

FOREIGN PATENT DOCUMENTS

| | | | |
|---|---|---|---|
| WO | 2020/051014 | * | 3/2020 |
| WO | 2020051014 | A1 | 3/2020 |

OTHER PUBLICATIONS

Patent Cooperation Treaty, International Search Report and Written Opinion for PCT/US2021/062069, 12 pages, dated Mar. 4, 2022.

* cited by examiner

ORAL FORMULATION OF A THERAPEUTIC COMPOUND

CROSS-REFERENCE TO RELATED APPLICATIONS

This application is a continuation of U.S. patent application Ser. No. 18/265,173, filed Jun. 2, 2023, which is a 35 U.S.C. § 371 application of International Application Serial No. PCT/US2021/062069, filed Dec. 6, 2021, which claims priority to U.S. Provisional Application No. 63/199,078 that was filed on Dec. 4, 2020. The entire content of the applications referenced above are hereby incorporated by reference herein.

FIELD OF THE INVENTION

The present invention is in the field of pharmaceutical compositions, specifically in the field of tablet compositions and more specifically in the field of immediate release tablet compositions.

BACKGROUND OF THE INVENTION

A major function of the gastrointestinal (GI) tract is to maintain intestinal water/sodium (Na+) homeostasis through a balance of secretory and absorption mechanisms. The Na+/hydrogen (H+) antiporter, referred to as sodium-hydrogen exchanger 3 (NHE3) plays a central role in the sodium uptake process. Tenapanor is an NHE3 inhibitor that acts locally in GI tract with minimal systemic bioavailability to inhibit the absorption of sodium from the lumen.

Tenapanor has also be shown clinically to lower serum phosphate in patients with hyperphosphatemia. Hyperphosphatemia is a serious condition resulting in an abnormally elevated level of phosphorus in the blood (greater than 5.5 mg/dL) which is often a co-morbidity of kidney disease, the organ responsible for elimination of phosphorus. Inhibition of NHE3 by tenapanor results in a conformational change of the GI epithelial cell junctions that significantly reducing paracellular uptake of phosphate at the primary pathway of phosphate absorption. Three successful Phase 3 studies demonstrating tenapanor's ability to reduce phosphate levels, as monotherapy and as part of a dual mechanism approach with phosphate binders, have been reported.

Despite treatment with phosphate binders (the only approved therapy for hyperphosphatemia), approximately 70% of CKD patients on dialysis continue to experience elevated phosphorus levels at any point in time (Spherix Global Insights: RealWorld Dynamix, Dialysis 2018). Phosphorus levels greater than 5.5 mg/dL have been shown to be an independent risk factor for cardiovascular morbidity and mortality in patients requiring dialysis (Block 2004), and internationally recognized treatment guidelines recommend lowering elevated phosphate levels toward the normal range (<4.6 mg/dL).

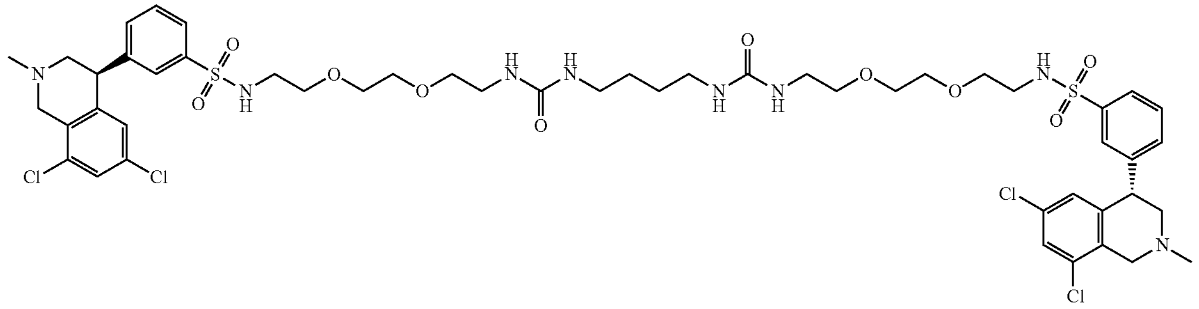

Tenapanor

Reduction of sodium uptake increases the fluid volume in the GI tract, which results in a softer fecal consistency and increased GI transit both in animals and in man. In its bis-HCl salt form, tenapanor has also been clinically shown to reduce abdominal pain in Irritable Bowel Syndrome with Constipation (IBS-C) patients. In an animal model of IBS-like colonic hypersensitivity, tenapanor reduced visceral hyperalgesia and normalized colonic sensory neuronal excitability and Transient Receptor Potential Vanilloid 1 (TRPV1) currents. TRPV1 is a well-known pain receptor that responds to a variety of noxious stimuli. Tenapanor attenuated the increase in permeability of human colonic epithelial monolayers to macromolecules caused by cytokines or human fecal supernatants. The beneficial effect of tenapanor on abdominal pain in patients with IBS-C may be a result of its ability to reduce colonic permeability to luminal macromolecules, which may reduce hyperexcitability of sensory neurons.

Figure 2:
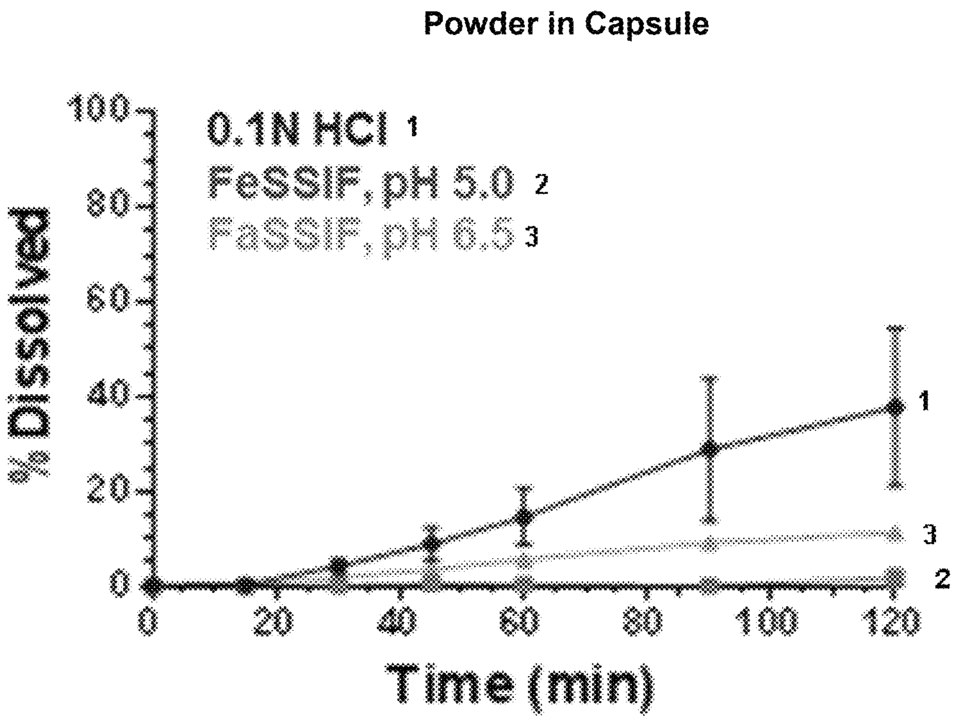

FIG. 2: Dissolution of capsule I, neat tenapanor HCl powder in HPMC capsules (Vcaps® from Capsugel®) in FaSSIF media pH 6.5, FeSSIF media pH 5 and in 0.1N HCl. Dissolution method: USP apparatus II (paddle), 75 rpm, 900 mL of media at 37° C.

Figure 3:
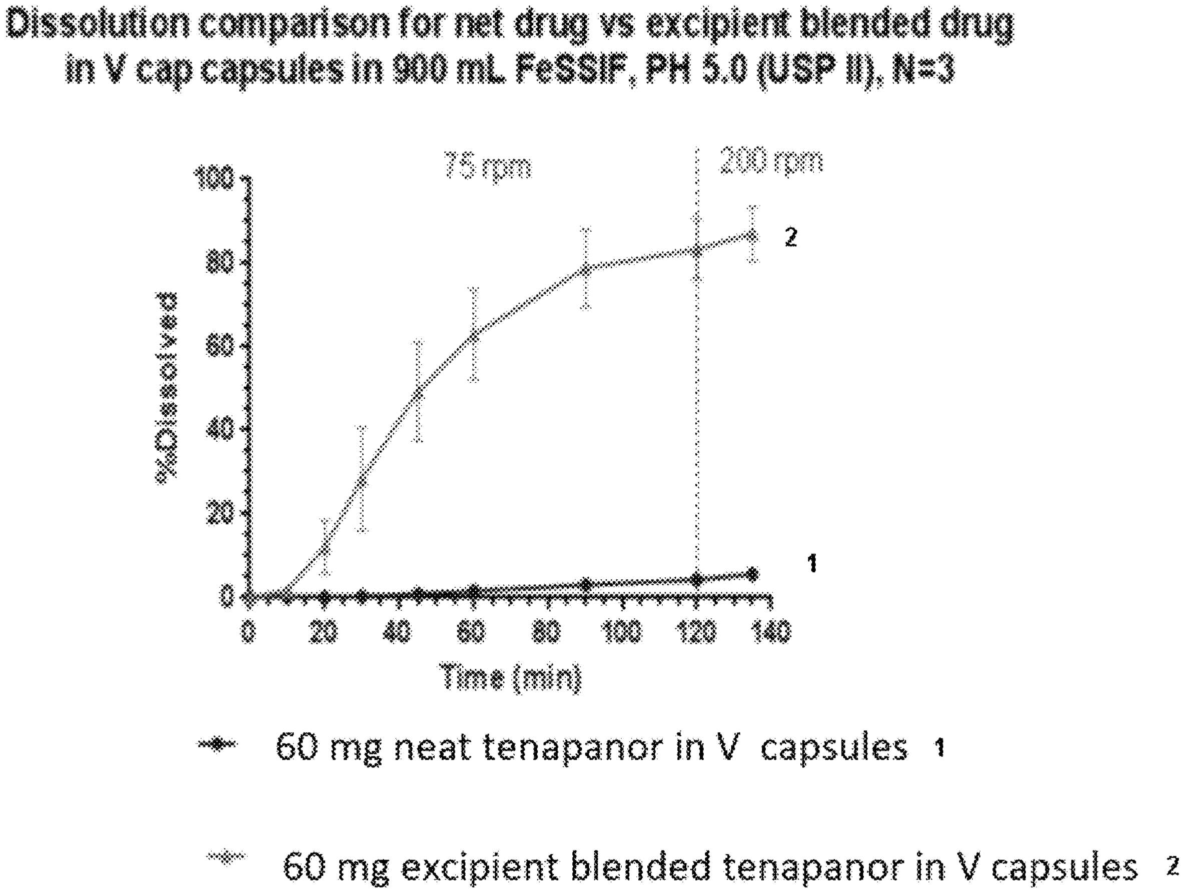

FIG. 3: Comparison of dissolution of capsule I (neat) and capsule II (excipient blended tenapanor HCl) in V capsules in FeSSIF media pH5.

Figure 4A:
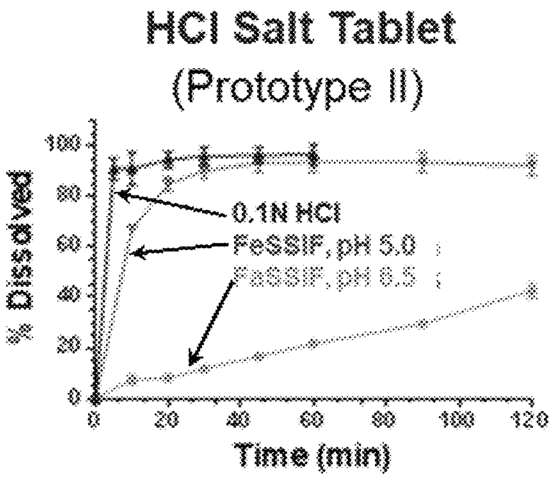
Figure 4B:
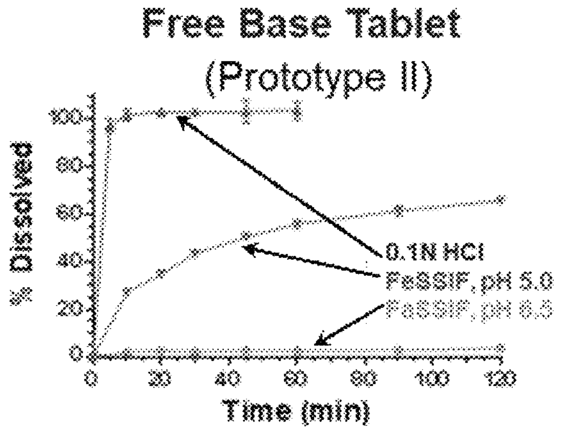
Figure 4C:
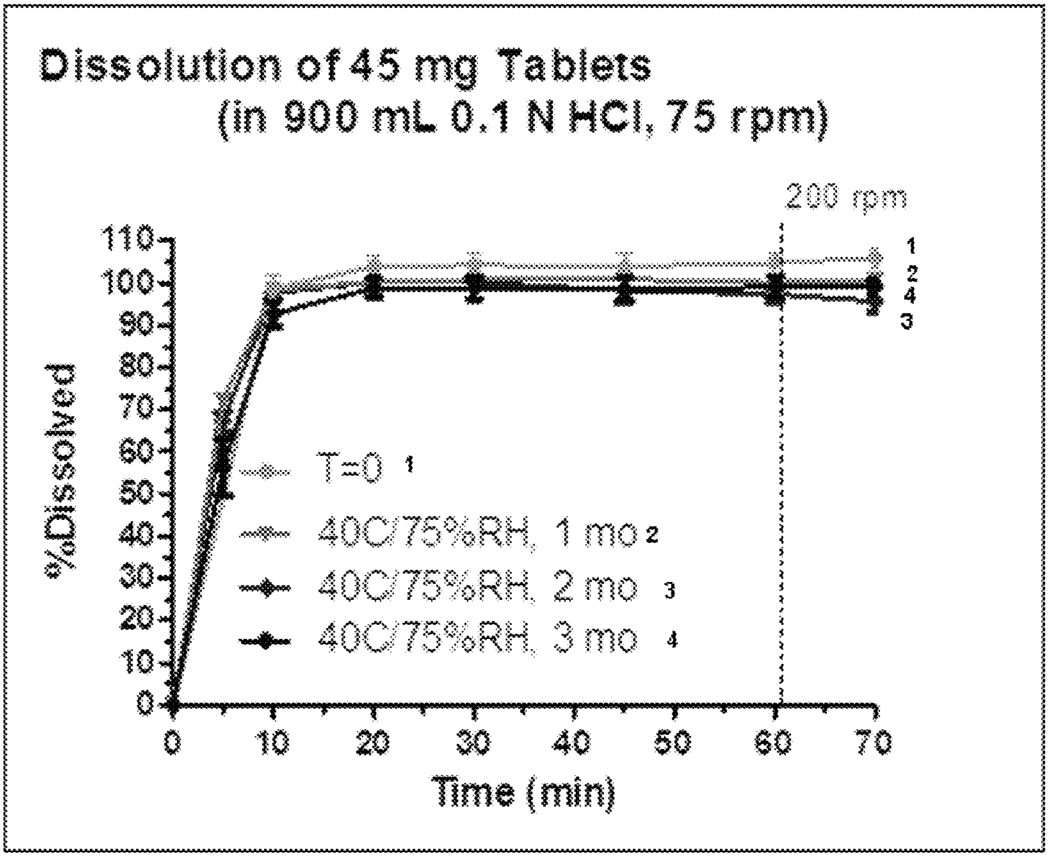

FIG. 4: Dissolution of prototype II tablets in FeSSIF pH 6.5 medium, FeSSIF pH 5 medium and in 0.1N HCl with 14 mg of tenapanor HCl (FIG. 4*a*); 14 mg tenapanor free base (FIG. 4*b*); and 50 mg of tenapanor HCl (FIG. 4*c*) in 0.1N HCl. Amount of tenapanor HCl expressed in base equivalents.

Figure 5:
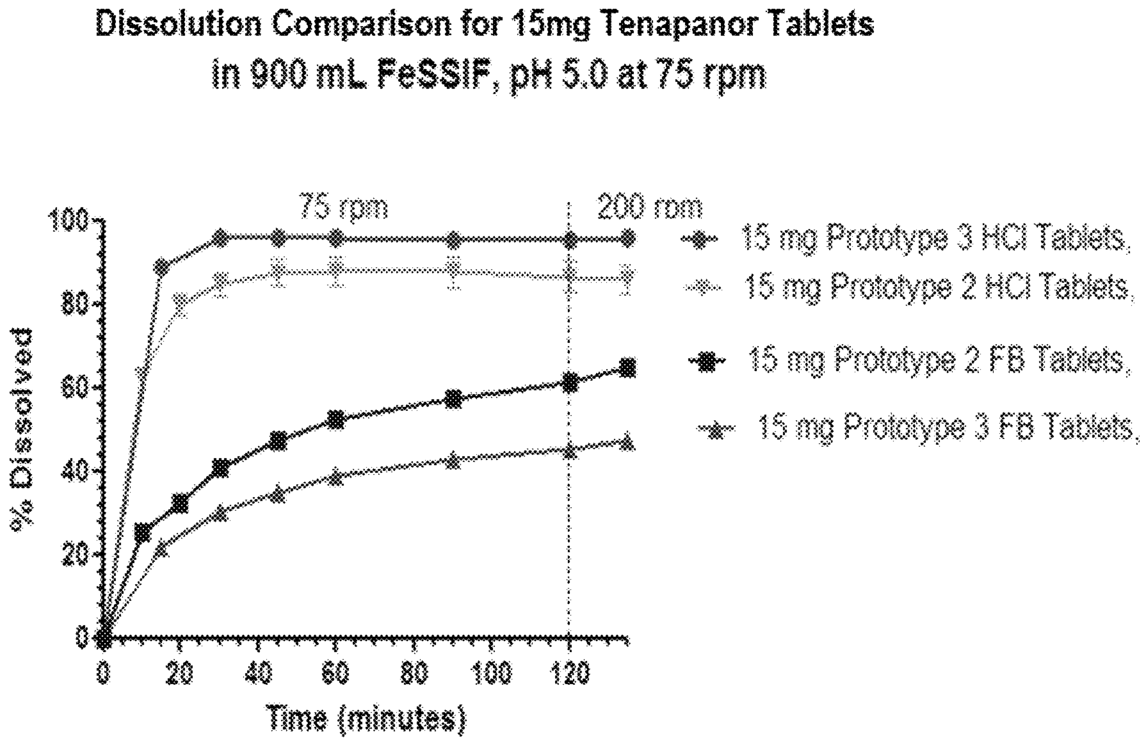

FIG. 5: Dissolution comparison of tenapanor free base and tenapanor HCl in 15 mg prototype II and prototype III tablets in FeSSIF pH 5.0.

Figure 6:
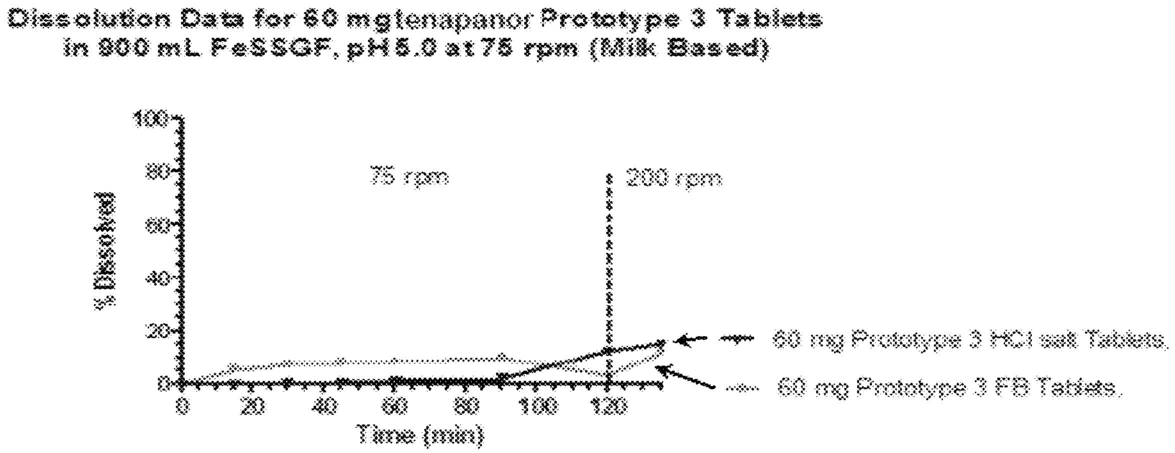
Figure 6:
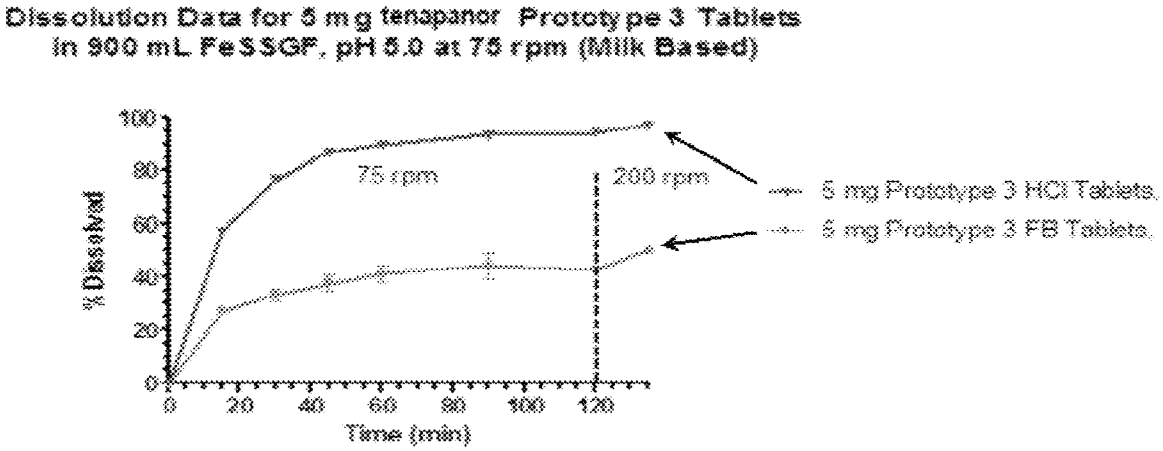

FIG. 6: Dissolution comparison of high (60 mg) and low (5 mg) loading of tenapanor free base and tenapanor HCl in prototype III tablets in FeSSGF medium at pH 5.0.

Figure 7:
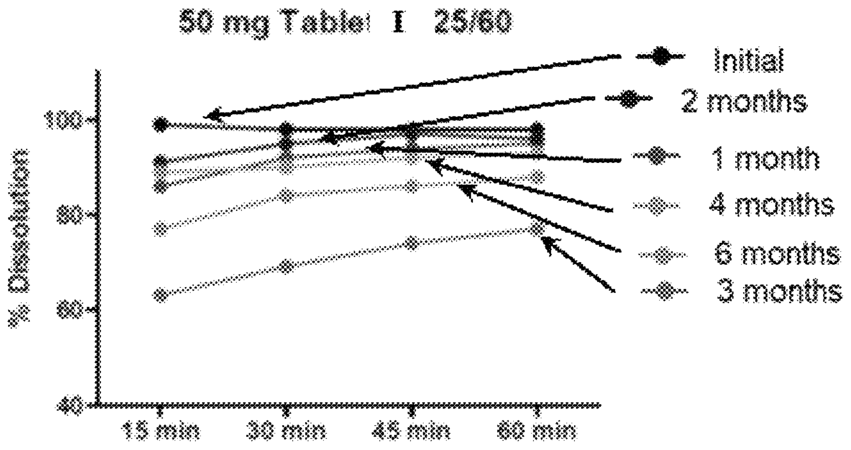
Figure 7:
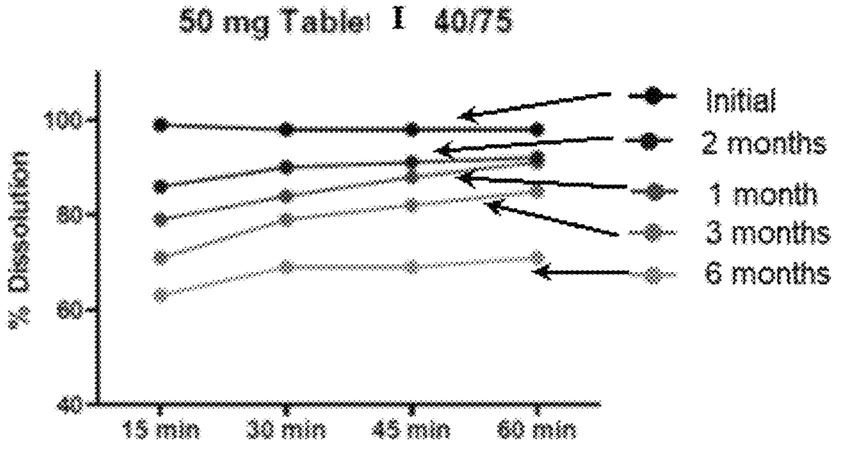

FIG. 7: Loss of dissolution performance in 0.1 N HCl. of prototype Ib tablet formulation over 6 months storage at 25° C./60% relative humidity, and 40° C./75% relative humidity.

Figure 8A:
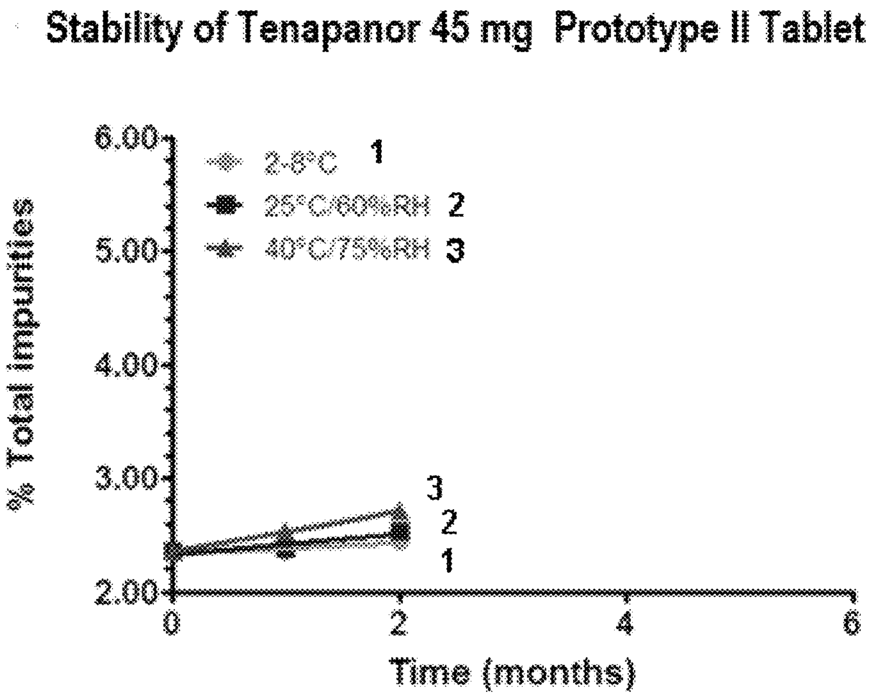
Figure 8B:
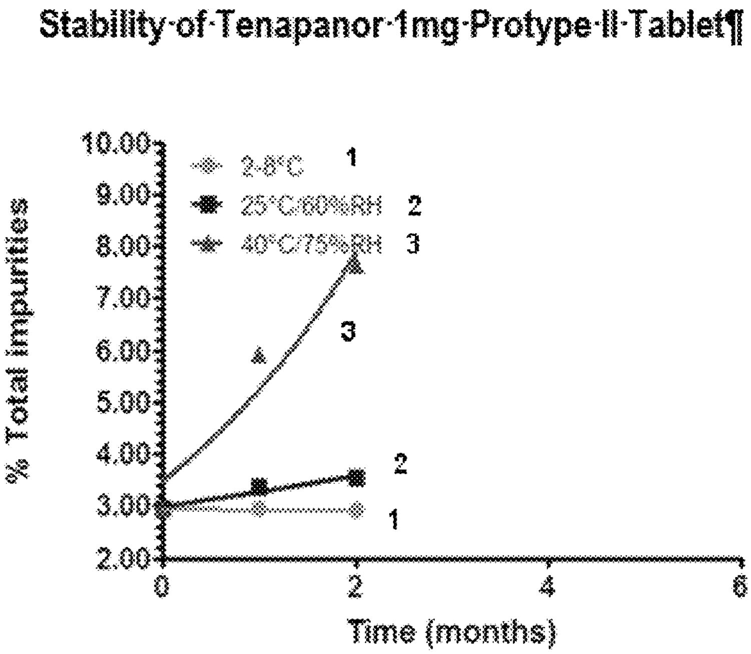

FIG. 8: Comparison of impurities over time at 2-8° C., 25° C./60% relative humidity, and 40° C./75% relative humidity of 45 mg (FIG. 8*a*) and 1 mg (FIG. 8*b*) loading of tenapanor in prototype II tablets.

Figure 9:
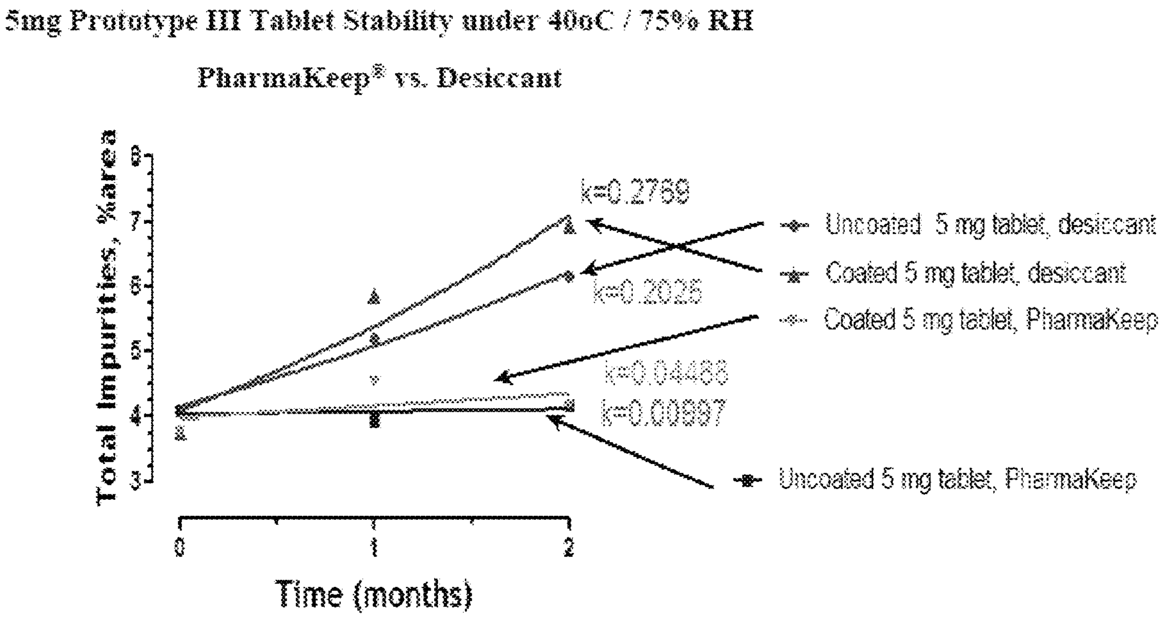

FIG. 9: Comparison of impurities of coated and uncoated 5 mg tenapanor prototype III tablets stored over time at 40° C./75% RH with a desiccant and with an oxygen absorbing desiccant (PharmaKeep®).

Figure 10:
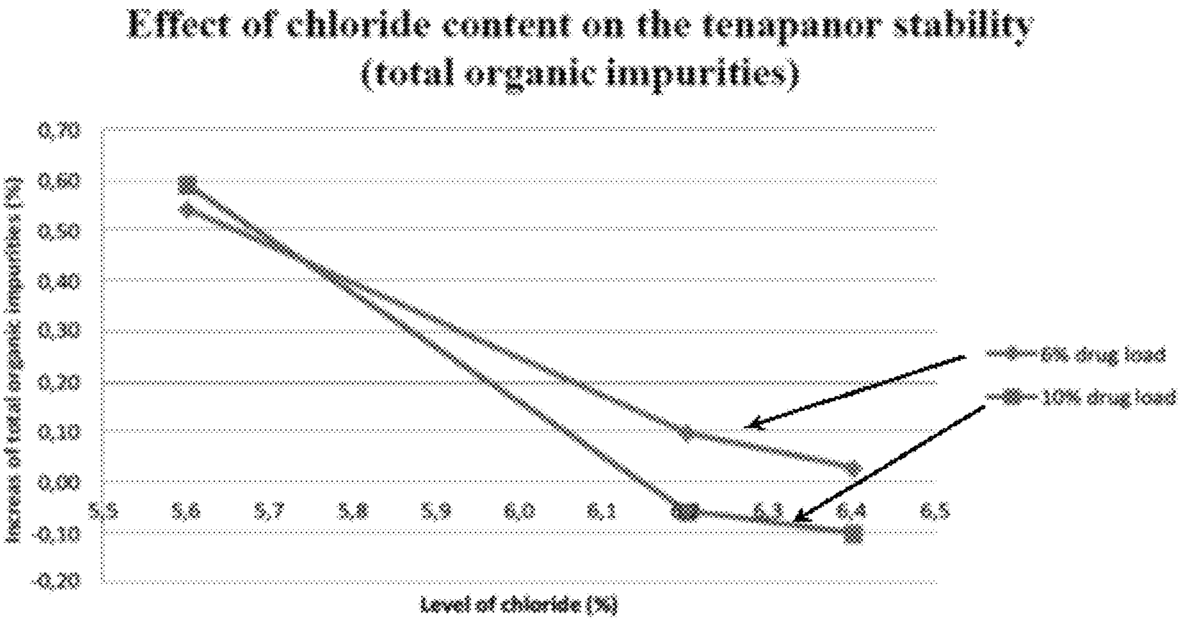

FIG. 10: Percent change in total impurities after one month open storage at 40° C./30% relative humidity versus chloride content for 6% and 10% loaded prototype III tenapanor HCl tablet formulations. Each tablet formulation contained 1% tartaric acid and 0.02% propyl gallate.

FS means fumed silica e.g. Cab-O-Sil®.

L-HPC means low substituted hydroxypropyl cellulose and also referred to as hydroxypropyl methylcellulose (HPMC) which is a disintegrant or disintegrating agent to aid in dissolution.

MCC means microcrystalline cellulose e.g. Avicel®.

PVP means N-vinyl-2-pyrrolidone crosslinked homopolymer e.g. Polyplasdone XLR.

SSF means sodium stearyl fumarate (e.g. Pruv®).

Tenapanor means the free-base compound 1-[2-[2-[2-[[3-[(4S)-6,8-dichloro-2-methyl-3,4-dihydro-1H-isoquinolin-4-yl]phenyl]sulfonylamino]ethoxy]ethoxy]ethyl]-3-[4-[2-[2-[2-[[3-[(4S)-6,8-dichloro-2-methyl-3,4-dihydro-1H-isoquinolin-4-yl]phenyl]sulfonylamino]ethoxy]ethoxy]ethylcarbamoylamino]butyl]urea. The bis-HCl (di-HCl) salt form of tenapanor is also interchangeably referred to as tenapanor hydrochloride or tenapanor HCl and has the following chemical structure:

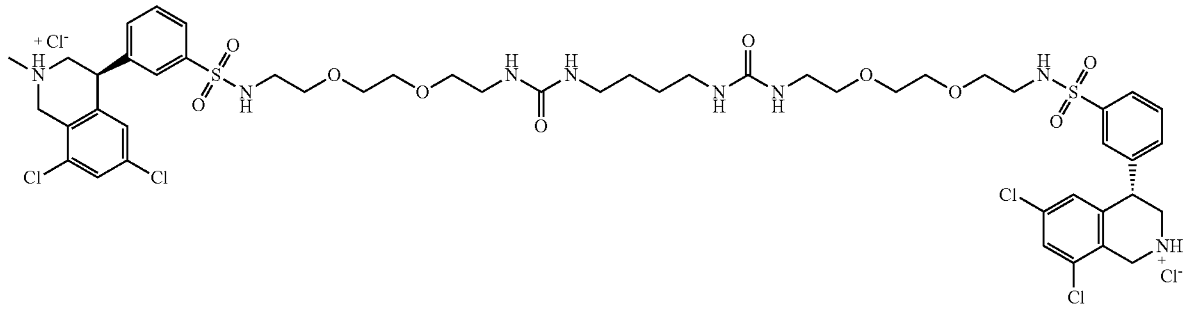

Tenapanor HCl

Figure 11A:
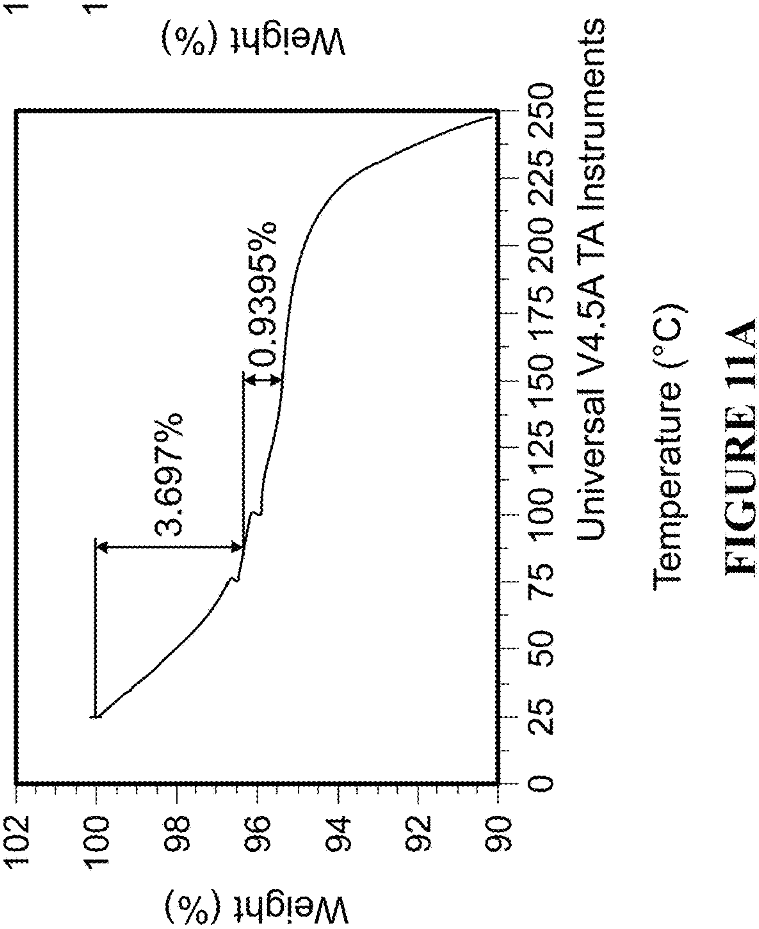
Figure 11B:
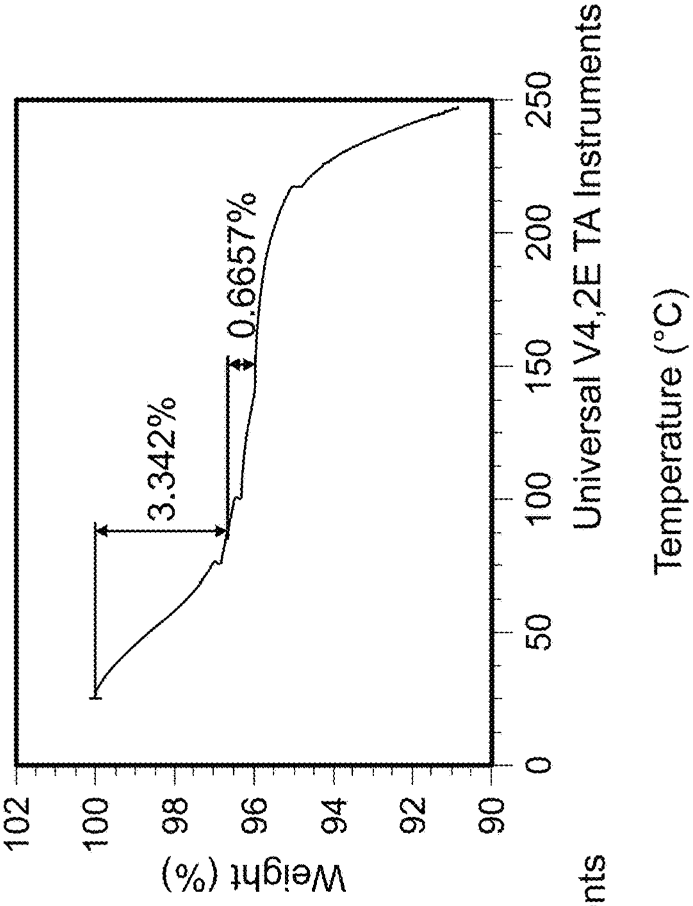

FIG. 11: Thermogravimetric analysis of spray-dried dispersion of tenapanor HCl at t (0) (panel A) and after five days exposed to ambient temperature and humidity (panel B). No significant differences between the traces indicated spray-dried dispersion of tenapanor HCl is in equilibrium with water.

Figure 12:
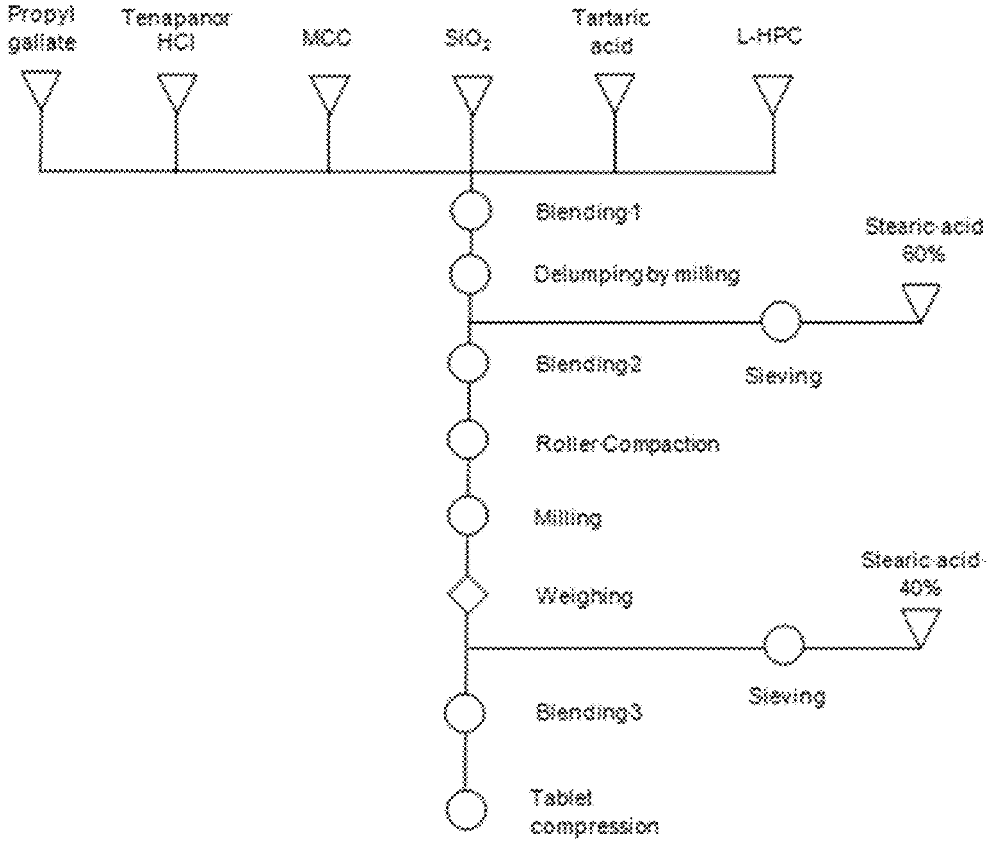

FIG. 12: Flow diagram of steps in formulating and tableting tenapanor.

DETAILED DESCRIPTION

Definitions

"% w/w" means the proportion of a particular component of the formulation, or when specified, the proportion of the component of the drug substance (API).

The term 'about' in the context of the amount of a particular formulation component means plus or minus 5% of the value to which it refers. For example, about 1% means 0.95% to 1.05%.

CSD means colloidal silicone dioxide.

Drug substance means the active pharmaceutical ingredient, tenapanor, also referred to as the API or active pharmaceutical ingredient.

FeSSGF mean Fed State Simulated Gastric Fluid media that simulates stomach fluids after a high-fat FDA meal which is compatible with USP apparatus.

FaSSIF means Fasted State Simulated Intestinal Fluid media that simulates intestinal fluids in a fasted state which is compatible with USP apparatus.

FeSSIF means Fed State Simulated Intestinal Fluid media that simulates intestinal fluids after a meal which is compatible with USP apparatus.

Figure 1:
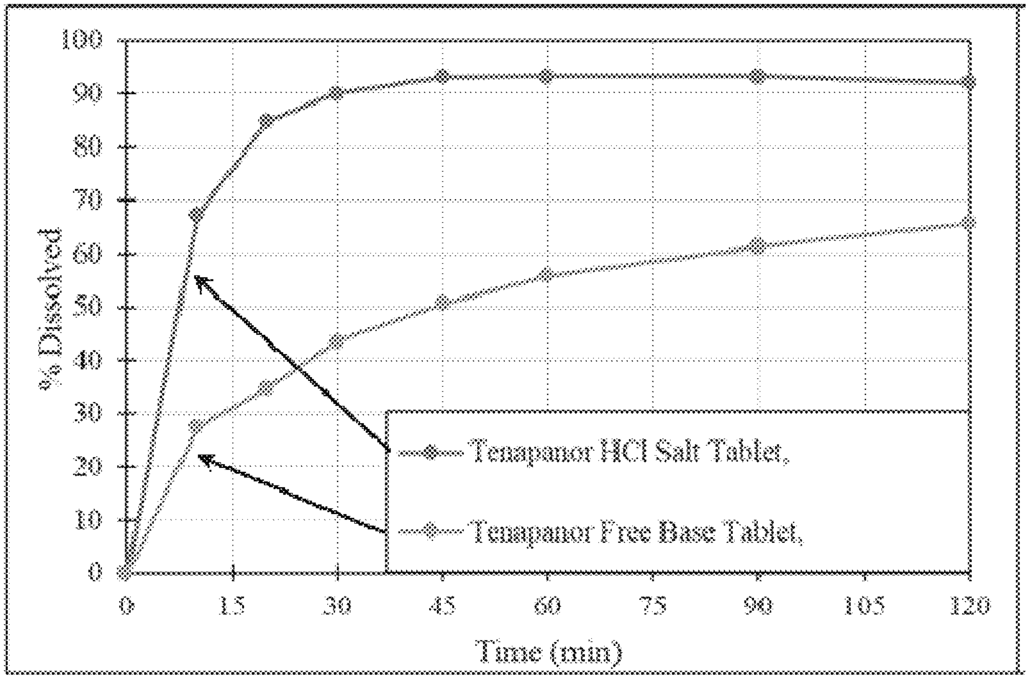
FIG. 1: Dissolution of 15 mg tenapanor HCl tablets and tenapanor free base tablets in FeSSIF media pH 5.0. Dissolution method: USP apparatus II (paddle), 75 rpm, 900 mL of media at 37° C.

A pharmacodynamic (PD) study (phase 1, single-center, randomized, 3-way cross-over, open-label study) evaluated the pharmacodynamics of different formulations of tenapanor in healthy volunteers taking omeprazole), was conducted to compare the difference in PD effect between the free base and hydrochloride salt of tenapanor in equivalent tablet formulations. As tenapanor is a locally acting, intestinally targeted NHE3 inhibitor, it was expected to influence absorption of sodium that resulted in higher levels of sodium excreted through the feces as opposed to urine. Tablets of the amorphous salt (15 mg, equivalent to 14 mg free base) and the crystalline free base (14 mg) were compared directly during formulation development using fecal and urine sodium as the PD markers in healthy volunteers who were also taking omeprazole as a proton pump inhibitor. These two tablet formulations displayed different dissolution profiles at pH 5.0 (FIG. 1). The higher solubility of the amorphous HCl salt resulted in a greater extent of dissolution at pH 5.0 as compared to the crystalline free base. The dissolution of higher strength free base (60 mg) tablets was also shown to be dependent on the pH of the media.

Dissolution

Several capsules and tablet prototypes were prepared and tested for various properties, but were found to be unsatisfactory in particular, dissolution and stability,. Below are the composition of some of the capsule and tablet formulations as well as maximum dissolution observed in 0.1N HCl, pH 5 FeSSIF media and pH 6 FaSSIF media. Tablets from the same prototype designation differed by tenapanor loading and salt/free-base form but had the same disintegrant, glidant and lubricant excipients in the same % w/w but varied in the % w/w of tenapanor and filler making up the remainder of tablet.

TABLE 1(a)-1(m)

Capsule and tablet prototype components and maximum observed percent dissolution in 0.1N HCl solution, pH 5 FeSSIF media and pH 6.5 FaSSIF media.

(a)

| CAPSULE I (60 mg) | function | % w/w | max % dis 0.1N HCL | max % dis pH 5 | max % dis pH 6.5 |
|---|---|---|---|---|---|
| tenapanor HCl | active | 100 | ~35 | ~0 | ~10 |
| — | disintegrant | 0 | | | |
| — | glidant | 0 | | | |
| — | lubricant | 0 | | | |
| — | filler | 0 | | | |

(b)

| CAPSULE II (5 mg) | function | % w/w | max % dis 0.1N HCL | max % dis pH 5 | max % dis pH 6.5 |
|---|---|---|---|---|---|
| tenapanor HCl | active | 1.5 | | | |
| — | disintegrant | 0 | | | |
| FS | glidant | 3.0 | | | |
| stearic acid | lubricant | 3.0 | | | |
| mannitol | filler | 92.4 | | | |

(c)

| CAPSULE II (60 mg) | function | % w/w | max % dis 0.1N HCL | max % dis pH 5 | max % dis pH 6.5 |
|---|---|---|---|---|---|
| tenapanor HCl | active | 21.5 | | ~85 | |
| — | disintegrant | 0 | | | |
| FS | glidant | 3.0 | | | |
| stearic acid | lubricant | 3.0 | | | |
| mannitol | filler | 72.5 | | | |

(d)

| PROTO I (50 mg) tablet | function | % w/w | max % dis 0.1N HCL | max % dis pH 5 | max % dis pH 6.5 |
|---|---|---|---|---|---|
| tenapanor HCl | active | 25.0 | ~95 | | |
| PVP | disintegrant | 5.0 | | | |
| FS | glidant | 1.0 | | | |
| SSF | lubricant | 2.0 | | | |
| MCC/CSD* | filler/glidant | 67.0 | | | |

(e)

| PROTO II-FB (14 mg) tablet | function | % w/w | max % dis 0.1N HCL | max % dis pH 5 | max % dis pH 6.5 |
|---|---|---|---|---|---|
| tenapanor (free base) | active | 5.8 | ~100 | ~65 | ~5 |
| PVP | disintegrant | 5.0 | | | |
| fumed silica | glidant | 1.0 | | | |
| Mg stearate | lubricant | 2.0 | | | |
| MCC/CSD* | filler/glidant | 86.2 | | | |

(f)

| PROTO II-HCl (14 mg) tablet | function | % w/w | max % dis 0.1N HCL | max % dis pH 5 | max % dis pH 6.5 |
|---|---|---|---|---|---|
| tenapanor HCl | active | 6.4 | ~95 | ~90 | ~45 |
| PVP | disintegrant | 5.0 | | | |
| fumed silica | glidant | 1.0 | | | |
| Mg stearate | lubricant | 2.0 | | | |
| MCC/CSD* | filler/glidant | 85.6 | | | |

TABLE 1(a)-1(m)-continued

Capsule and tablet prototype components and maximum observed percent dissolution in 0.1N HCl solution, pH 5 FeSSIF media and pH 6.5 FaSSIF media.

(g)

| PROTO II - HCl (45 mg) tablet | function | % w/w | max % dis 0.1N HCL | max % dis pH 5 | max % dis pH 6.5 |
|---|---|---|---|---|---|
| tenapanor HCl | active | 24.1 | ~95 | | |
| PVP | disintegrant | 5.0 | | | |
| fumed silica | glidant | 1.0 | | | |
| Mg stearate | lubricant | 2.0 | | | |
| MCC/CSD* | filler/glidant | 67.9 | | | |

(h)

| PROTO III FB (5 mg) tablet | function | % w/w | max % dis 0.1N HCL | max % dis pH 5 | max % dis pH 6.5 |
|---|---|---|---|---|---|
| tenapanor FB | active | 5 | | ~50*** | |
| L-HPC | disintegrant | 15 | | | |
| FS | glidant | 1.0 | | | |
| stearic acid | lubricant | 5.0 | | | |
| MCC/mannitol** | filler | 74 | | | |

(i)

| PROTO III HCl (5 mg) tablet | function | % w/w | max % dis 0.1N HCL | max % dis pH 5 | max % dis pH 6.5 |
|---|---|---|---|---|---|
| tenapanor HCl | active | 5 | | ~95*** | |
| L-HPC | disintegrant | 15 | | | |
| FS | glidant | 1.0 | | | |
| stearic acid | lubricant | 5.0 | | | |
| MCC/mannitol** | filler | 74 | | | |

(j)

| PROTO III HCl (15 mg) tablet | function | % w/w | max % dis 0.1N HCL | max % dis pH 5 | max % dis pH 6.5 |
|---|---|---|---|---|---|
| tenapanor HCl | active | | | ~95 | |
| L-HPC | disintegrant | 15 | | | |
| FS | glidant | 1.0 | | | |
| stearic acid | lubricant | 5.0 | | | |
| MCC/mannitol** | filler | | | | |

(k)

| PROTO III FB (15 mg) tablet | function | % w/w | max % dis 0.1N HCL | max % dis pH 5 | max % dis pH 6.5 |
|---|---|---|---|---|---|
| tenapanor HCl | active | | | ~40 | |
| L-HPC | disintegrant | 15 | | | |
| FS | glidant | 1.0 | | | |
| stearic acid | lubricant | 5.0 | | | |
| MCC/mannitol** | filler | | | | |

(l)

| PROTO III FB (60 mg) tablet | function | % w/w | max % dis 0.1N HCL | max % dis pH 5 | max % dis pH 6.5 |
|---|---|---|---|---|---|
| tenapanor FB | active | 22.2 | ~95 | ~70 | |
| L-HPC | disintegrant | 15 | | | |
| FS | glidant | 1.0 | | | |
| stearic acid | lubricant | 5.0 | | | |
| MCC/mannitol** | filler | 56.8 | | | |

TABLE 1(a)-1(m)-continued

Capsule and tablet prototype components and maximum observed percent dissolution in 0.1N HCl solution, pH 5 FeSSIF media and pH 6.5 FaSSIF media.

(m)

| PROTO III (60 mg) tablet | function | % w/w | max % dis 0.1N HCL | max % dis pH 5 | max % dis pH 6.5 |
|---|---|---|---|---|---|
| tenapanor FB, HCl | active | 22.2 | | ~15*** | |
| L-HPC | disintegrant | 15 | | | |
| FS | glidant | 1.0 | | | |
| stearic acid | lubricant | 5.0 | | | |
| MCC/mannitol** | filler | 56.8 | | | |

*co-processed MCC and CSD e.g. ProSolv ® SMCC HP

**e.g. Pearlitol ®

***in FeSSGF (all other pH 5 in FeSSIF media)

From the dissolution experiments of the capsule and tablet formulations in tables 1 (a) to 1 (m), it was observed that:

- Tenapanor required formulating to achieve acceptable dissolution, as illustrated in FIG. 2 where only about 40% of neat tenapanor dissolved after 120 minutes in low pH. At pH 5.0 neat tenapanor capsules demonstrated negligible dissolution whereas tenapanor in identical capsules but blended with a glidant, lubricant and filler (capsule II) demonstrated about 85% dissolution.
- Tenapanor had better dissolution at low pH.
- Tenapanor HCl salt form had superior dissolution at higher pH compared to the free base, as illustrated in FIG. 1. This was also demonstrated in prototype II tablets (FIG. 4*a* v. FIG. 4*b*) at high pH 5 and 6.5 and by prototype III tablets (FIG. 5).
- High loading of tenapanor negatively affected dissolution. For example, 60 mg prototype III tablets with 22.2% w/w demonstrated negligible dissolution in pH 5 media whereas 5 mg prototype III tablets with 5% w/w demonstrated about 40% dissolution for free-base version and about 95% for the HCl version.

Based on the forgoing results, prototype III was determined to have superior dissolution properties compared to prototype II, as illustrated in FIG. 5, and was chosen for further development and stability studies. Prototype I tablets demonstrated reasonable dissolution in 0.1N HCl (about 95% after 60 min), however, this significantly declined as the formulation aged as illustrated in FIG. 7.

Chemical Stability

Prototype III tablet formulation was studied for chemical stability. A 5 mg tenapanor prototype III tablet formulation was stored under accelerated stability conditions of elevated temperature and relative humidity. After two months the formulation contained significantly elevated degradant impurities. Analysis by reverse phase liquid chromatography identified the following impurities:

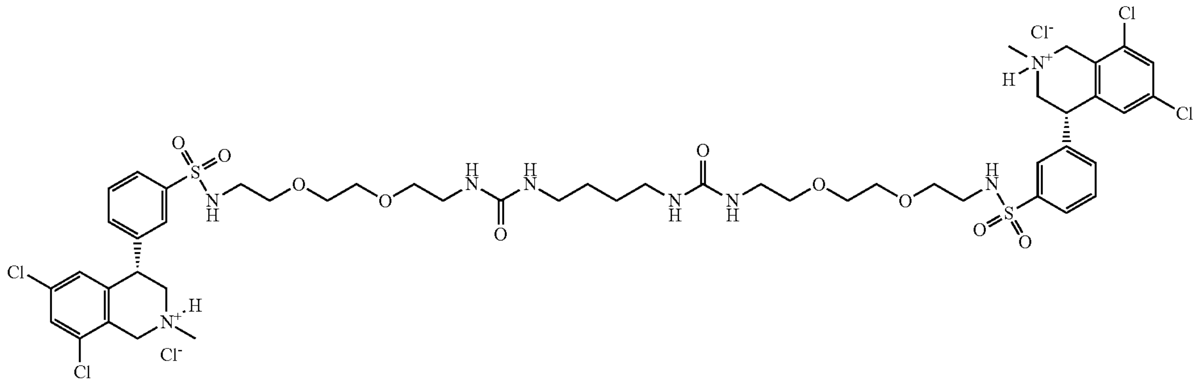

tenapanor HCl

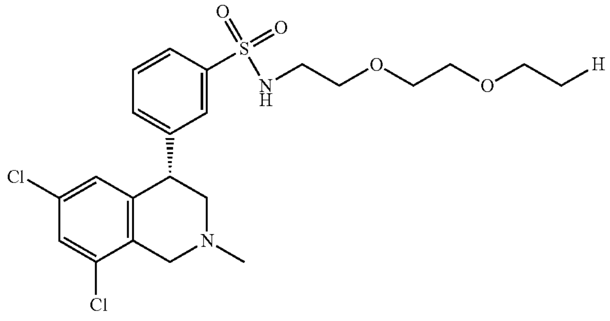

tenap-B

-continued

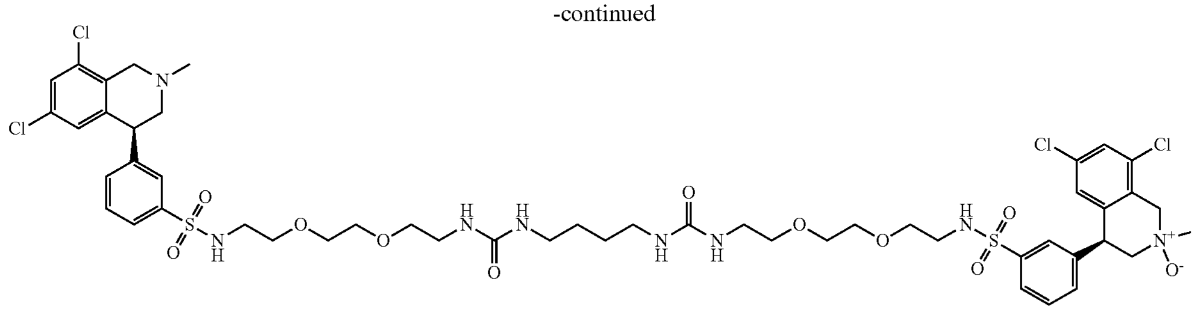

tenap-N-oxide

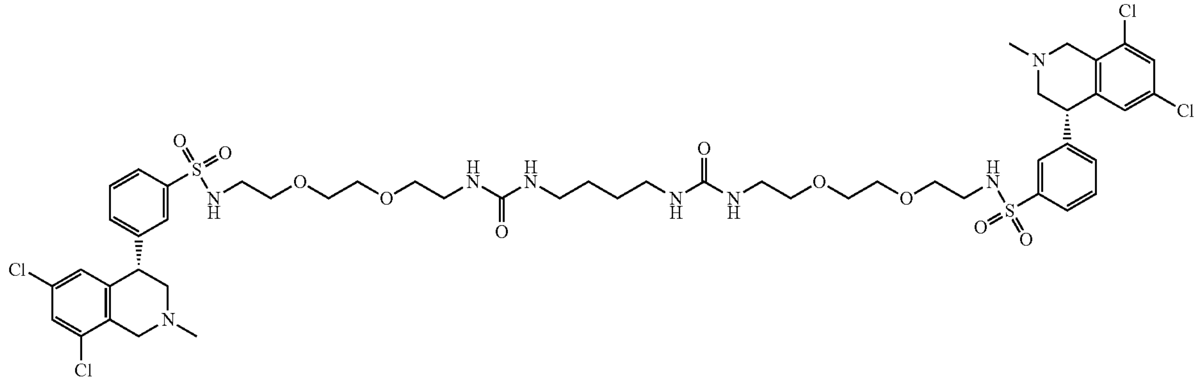

tenap-D

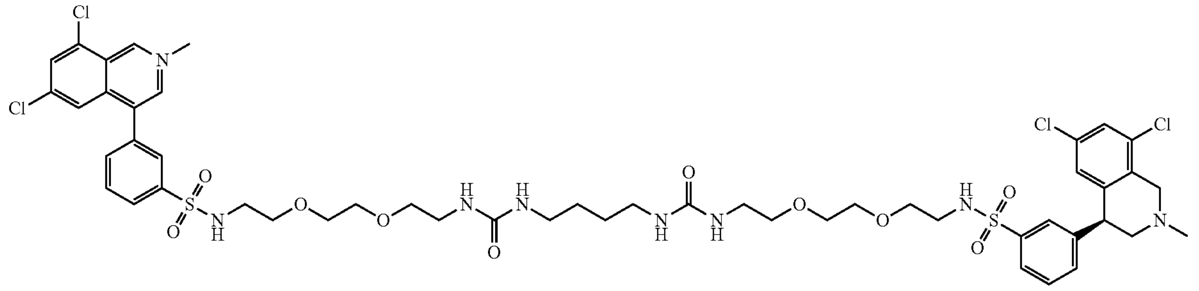

isoquinolinium

In performing these studies, it was observed that the presence of a desiccant cannister that also contained an oxygen absorbent remained chemically stable over two months under these conditions whereas the same tablets in the presence of a desiccant canister without oxygen absorbent had significantly elevated degradant impurity content. See FIG. 9. Based on this observation, prototype III tablet containing an antioxidant were made and tested. Also investigated was the impact of chloride levels on the chemical stability of tenapanor tablets. Tables 2 and 3 show percent change in organic impurities denoted tenap-B, tenap-D, tenap-N-oxide and isoquinolinium after one month and 2.5 months of open storage in elevated temperature and relative humidity.

TABLE 2

Percent change in impurities after 1 month open storage in 40° C./30% RH of prototype III formulations

| tablet ID | % w/w Cl | PG | TA | DL | total impurities | tenap-B | tenap-D | isoquin | tenap-N-oxide |
|---|---|---|---|---|---|---|---|---|---|
| N1 | 5.6 | 0 | 0 | 6 | 1.59 | 0.08 | 0.04 | 0.43 | 0.41 |
| N2 | 6.4 | 0 | 0 | 10 | −0.02 | 0.00 | 0.00 | 0.01 | 0.00 |
| N3 | 5.6 | 0.2 | 0 | 10 | 0.35 | 0.00 | 0.09 | 0.18 | 0.25 |
| N4 | 6.4 | 0.2 | 0 | 6 | −0.05 | 0.00 | 0.03 | 0.03 | 0.00 |
| N5 | 5.6 | 0 | 1 | 10 | 0.51 | 0.00 | 0.03 | 0.11 | 0.17 |
| N6 | 6.4 | 0 | 1 | 6 | 0.03 | 0.00 | 0.00 | 0.03 | 0.00 |
| N7 | 5.6 | 0.2 | 1 | 6 | 0.54 | 0.00 | 0.13 | 0.22 | 0.25 |
| N8 | 6.4 | 0.2 | 1 | 10 | −0.10 | 0.00 | −0.02 | 0.00 | 0.00 |
| N9 | 6.2 | 0.2 | 1 | 6 | 0.10 | 0.00 | 0.08 | 0.05 | 0.07 |

TABLE 2-continued

Percent change in impurities after 1 month open storage in 40° C./30% RH of prototype III formulations

| tablet ID | % w/w Cl | PG | TA | DL | total impurities | tenap-B | tenap-D | isoquin | tenap-N-oxide |
|---|---|---|---|---|---|---|---|---|---|
| N10 | 6.2 | 0.2 | 1 | 6 | −0.04 | 0.00 | 0.06 | 0.05 | 0.01 |
| N12 | 6.2 | 0.2 | 1 | 6 | −0.03 | 0.00 | 0.04 | 0.02 | 0.02 |
| N13 | 5.6 | 0.05 | 1 | 6 | 0.50 | 0.00 | 0.07 | 0.20 | 0.23 |
| N14 | 5.6 | 0.4 | 1 | 6 | 0.55 | 0.00 | 0.19 | 0.19 | 0.32 |
| N15 | 5.6 | 0.05 | 0 | 10 | 0.71 | 0.00 | 0.06 | 0.18 | 0.24 |
| N16 | 5.6 | 0.4 | 0 | 10 | 0.44 | 0.00 | 0.14 | 0.15 | 0.31 |
| N17 | 5.6 | 0.05 | 1 | 10 | 0.22 | 0.00 | 0.04 | 0.11 | 0.16 |
| N18 | 5.6 | 0.4 | 1 | 10 | 0.34 | 0.00 | 0.12 | 0.11 | 0.20 |
| N20 | 5.6 | 0 | 1 | 6 | 2.20 | 0.13 | 0.12 | 0.38 | 0.27 |
| N21 | 6.4 | 0.2 | 1 | 6 | 0.03 | 0.03 | 0.03 | 0.03 | 0.00 |
| N22 | 5.6 | 0.2 | 1 | 10 | 0.59 | 0.06 | 0.15 | 0.14 | 0.13 |
| N23 | 6.2 | 0.2 | 1 | 10 | −0.06 | 0.06 | 0.02 | 0.02 | −0.06 |
| N24 | 5.6 | 0 | 0 | 10 | 2.17 | 0.11 | 0.08 | 0.34 | 0.35 |
| N25 | 6.4 | 0.4 | 0 | 6 | 0.24 | 0.04 | 0.12 | 0.05 | 0.00 |
| N26 | 6.4 | 0.05 | 0 | 10 | −0.08 | 0.02 | −0.02 | 0.02 | 0.00 |
| N27 | 6.4 | 0.4 | 0 | 10 | 0.05 | 0.08 | −0.02 | 0.01 | 0.05 |
| N28 | 5.6 | 0 | 0 | 10 | 2.23 | 0.15 | 0.08 | 0.36 | 0.38 |

TABLE 3

Percent change in impurities after 2.5 months open storage in 40° C./30% RH of prototype III formulations

| tablet ID | % w/w Cl | PG | TA | DL | total impurities | tenap-B | tenap-D | isoquin | tenap-N-oxide |
|---|---|---|---|---|---|---|---|---|---|
| N1 | 5.6 | 0 | 0 | 6 | 3.91 | 0.20 | 0.07 | 0.85 | 0.94 |
| N2 | 6.4 | 0 | 0 | 10 | 0.07 | 0.00 | 0.00 | 0.01 | 0.06 |
| N3 | 5.6 | 0.2 | 0 | 10 | 1.80 | 0.06 | 0.14 | 0.54 | 0.72 |
| N4 | 6.4 | 0.2 | 0 | 6 | 0.25 | 0.00 | 0.06 | 0.07 | 0.07 |
| N5 | 5.6 | 0 | 1 | 10 | 1.82 | 0.11 | 0.04 | 0.26 | 0.40 |
| N6 | 6.4 | 0 | 1 | 6 | 0.17 | 0.05 | 0.00 | 0.04 | 0.06 |
| N7 | 5.6 | 0.2 | 1 | 6 | 1.90 | 0.00 | 0.21 | 0.55 | 0.68 |
| N8 | 6.4 | 0.2 | 1 | 10 | 0.06 | 0.05 | −0.02 | 0.01 | 0.08 |
| N9 | 6.2 | 0.2 | 1 | 6 | 0.68 | 0.00 | 0.15 | 0.14 | 0.14 |
| N10 | 6.2 | 0.2 | 1 | 6 | 0.62 | 0.00 | 0.14 | 0.14 | 0.08 |
| N12 | 6.2 | 0.2 | 1 | 6 | 0.56 | 0.00 | 0.12 | 0.12 | 0.07 |
| N20 | 5.6 | 0 | 1 | 6 | 3.65 | 0.23 | 0.18 | 0.60 | 0.51 |
| N21 | 6.4 | 0.2 | 1 | 6 | 0.25 | 0.03 | 0.12 | 0.03 | 0.06 |
| N22 | 5.6 | 0.2 | 1 | 10 | 1.66 | 0.06 | 0.34 | 0.37 | 0.41 |
| N24 | 5.6 | 0 | 0 | 10 | 3.47 | 0.20 | 0.13 | 0.55 | 0.67 |
| N25 | 6.4 | 0.4 | 0 | 6 | 1.14 | 0.06 | 0.31 | 0.12 | 0.08 |
| N26 | 6.4 | 0.05 | 0 | 10 | −0.02 | 0.02 | −0.02 | 0.01 | 0.06 |
| N27 | 6.4 | 0.4 | 0 | 10 | 0.17 | 0.07 | 0.04 | 0.00 | 0.05 |
| N28 | 5.6 | 0 | 0 | 10 | 3.68 | 0.20 | 0.13 | 0.54 | 0.68 |

Cl = chloride content in amorphous solid tenapanor drug substance from spray drying.
PG and TA = propyl gallate and tartaric acid content of total formulation
drug loading = tenapanor HCl content (free base equivalents) in total formulation
tenap-B = degradation product
tenap-D = degradation product
isoquin = isoquinolinium degradation product
tenap-N-oxide = degradation product Effect of Antioxidant At lower drug loading (6% w/w) and lower chloride content of the drug substance (5.6% w/w), the presence of an antioxidant improved stability but had no additional stabilizing effect at higher drug loading (10% w/w). For example, N3 tablets with 0.2% propyl gallate and low drug loading showed 0.35% impurity increase after 1 month compared to a 2.23% increase for N28 tablets having no antioxidant present but otherwise identical. However at 10% w/w drug loading, N26 and N27 tablets having 0.05% and 0.4% propyl gallate were no improvement over N2 tablets without propyl gallate.

Effect of Additional Acidifier

The addition of an acidifier was found to improve chemical stability when drug substance chloride content was stoichiometric. For example, N5 tablets with 1% tartaric acid showed increases of 0.51% and 2.23% after one and 2.5 months respectively, whereas N28 tablets without tartaric acid showed higher increases in impurities of 2.23% and 3.68%. However, for tablets made drug substance having super-stoichiometric chloride content, addition of an acidifier had no effect on chemical stability. For example, N21 tablets made with drug substance having 6.5% w/w chloride content and 1% tartaric acid had the same increases of impurities after one month and 2.5 months as the same tablet formulation without tartaric acid.

Effect of Chloride Content

The stoichiometric content of chloride in the tenapanor drug substance, i.e. a 2:1 ratio to tenapanor, is 5.82% w/w. It was observed that drug substance chloride content of greater than the stoichiometric ratio reduced the emergence of organic impurities over time. In particular, 6.4% drug substance chloride content demonstrated marked stability regardless of drug loading, the presence of an antioxidant or an additional acidifying agent. For example, N2 tablets containing the same drug load (and no antioxidant or additional acidifying agent) as N28 tablets, but higher drug substance chloride content, showed no increase in total impurities after one month and only 0.07% increase after 2.5 months. On the other hand, N28 tablets with low drug substance chloride content showed increases of 2.23% and 3.68% after one and 2.5 months, respectively. A similar effect was observed in the presence of antioxidant (N7 tablets v N21 tablets) or added acidifying agent (N6 tablets v N20 tablets).

The results shown in tables 1-3 show that the optimum balance of dissolution and stability properties was achieved with a tablet formulation containing greater than about 6% w/w of tenapanor HCl with a chloride content that is greater than 2:1 stoichiometry. 2:1 stoichiometry corresponds to 5.82% chloride content of the drug substance. Accordingly, an aspect of the presentation is a pharmaceutical composition comprising greater than about 6% w/w of tenapanor bis-HCl as an active ingredient and a pharmaceutically acceptable excipient, wherein the total chloride content of said active ingredient is greater than 5.82%. In an embodiment, the chloride content of said drug substance is from about 6.0% to about 6.8% w/w. In an embodiment, the chloride content is about 6.1%. In an embodiment, the chloride content is about 6.2%. In an embodiment, the chloride content is about 6.3%. In an embodiment, the chloride content is about 6.4%. In an embodiment, the chloride content is about 6.5%. In an embodiment, the chloride content is about 6.6%. In an embodiment, the chloride content is about 6.7%. In an embodiment, the chloride content is about 6.8%. In an embodiment, the chloride content is about 6.9%. In an embodiment, the chloride content is 6.4%.

In another aspect of the invention there is provided a pharmaceutical formulation comprising greater than about 6% w/w of the bis-HCl salt of tenapanor, wherein the total amount of HCl in the formulation is greater than twice the molar ratio to tenapanor. In an embodiment, the total amount of HCl in the formulation is from 2.1 to 3 times the molar ratio to tenapanor. In an embodiment, the total amount of HCl in the formulation is 2.1 times the molar ratio to tenapanor. In an embodiment, the total amount of HCl in the formulation is 2.2 times the molar ratio to tenapanor. In an embodiment, the total amount of HCl in the formulation is 2.3 times the molar ratio to tenapanor. In an embodiment, the total amount of HCl in the formulation is 2.4 times the molar ratio to tenapanor. In an embodiment, the total amount of HCl in the formulation is 2.5 times the molar ratio to tenapanor. In an embodiment, the total amount of HCl in the formulation is 2.6 times the molar ratio to tenapanor. In an embodiment, the total amount of HCl in the formulation is 2.7 times the molar ratio to tenapanor. In an embodiment, the total amount of HCl in the formulation is 2.8 times the molar ratio to tenapanor. In an embodiment, the total amount of HCl in the formulation is 2.9 times the molar ratio to tenapanor. In an embodiment, the total amount of HCl in the formulation is 3 times the molar ratio to tenapanor.

In an embodiment of the pharmaceutical formulations of the invention, tenapanor is in amorphous solid form. In another embodiment, tenapanor is a spray-dried dispersion. tenapanor is in free base solid form. In another embodiment, tenapanor is in bis-hydrochloride salt form. In another embodiment, tenapanor is an amorphous solid in bis-hydrochloride salt form.

In another embodiment of the pharmaceutical formulations of the invention, tenapanor is present in an amount of about 6% to 10% w/w. In another embodiment, tenapanor is present in an amount of about 6% w/w. In another embodiment, tenapanor is present in an amount of about 7% w/w. In another embodiment, tenapanor is present in an amount of about 8% w/w. In another embodiment, tenapanor is present in an amount of about 9% w/w. In another embodiment, tenapanor is present in an amount of about 10% w/w. In another embodiment, tenapanor is present in an amount of about 11% w/w. In another embodiment, tenapanor is present in an amount of about 12% w/w. In another embodiment, tenapanor is present in an amount of about 13% w/w. In another embodiment, tenapanor is present in an amount of about 14% w/w. In another embodiment, tenapanor is present in an amount of about 15% w/w. In another embodiment, tenapanor is present in an amount of about 20% w/w. In another embodiment, tenapanor is present in an amount of about 25% w/w.

In another embodiment, pharmaceutical formulations of the invention further comprise an acidifying agent. In an embodiment, the acidifying agent is present in an amount of about 0.5% w/w to about 3% w/w. In an embodiment, the acidifying agent is citric acid, tartaric acid, fumaric acid, succinic acid, ascorbic acid, adipic acid, sorbic acid, glutaric acid and malic acid.

In an embodiment, the acidifying agent is tartaric acid. In an embodiment, the tartaric acid is present in an amount of about 0.5% w/w to about 3% w/w. In an embodiment, the tartaric acid is present in an amount of about 1% w/w. In an embodiment, the tartaric acid is present in an amount of 1% w/w.

In another embodiment, pharmaceutical formulations of the invention further comprise an antioxidant. In an embodiment, the antioxidant is selected from the group consisting of ascorbyl palmitate, butylated hydroxyanisole, butylated hydroxytoluene, calcium stearate, anhydrous citric acid, citric acid monohydrate, cysteine, potassium metabisulfite, propyl gallate, sodium metabisulfite, sodium thiosulfate pentahydrate, vitamin E and 3,4-dihydroxybenzoic acid. In an embodiment, the antioxidant is propyl gallate. In an embodiment, the antioxidant is present in the amount of about 0.01 to about 1.0% w/w. In an embodiment, the antioxidant is propyl gallate. In an embodiment, propyl gallate is present in the amount of about 0.1 to 0.5% w/w. In an embodiment, the propyl gallate is present in an amount of about 0.05% w/w. In an embodiment, the propyl gallate is present in an amount of about 0.2% w/w. In an embodiment, the propyl gallate is present in an amount of about 0.4% w/w. In an embodiment, the propyl gallate is present in an amount of 0.2% w/w.

In another embodiment, pharmaceutical formulations of the invention further comprise a disintegrant. In an embodiment, the disintegrant is selected from the group consisting of crospovidone, croscarmellose sodium, sodium starch, glycolate, gelatin, cellulose, a cellulose derivative and sucrose. In an embodiment, the disintegrant is a cellulose derivative. In an embodiment, the disintegrant is a low-substituted hydroxypropyl cellulose (L-HPC), alternatively referred to as hydroxypropyl methylcellulose. In an embodiment, the disintegrant is present in an amount from about 1% w/w to about 20% w/w. In an embodiment, the disintegrant is present in an amount from about 5% w/w to about 15% w/w. In an embodiment, the disintegrant is hydroxypropyl methylcellulose present in an amount of about 5% w/w. In an embodiment, the hydroxypropyl methylcellulose is present in an amount of 5% w/w.

In another embodiment, the pharmaceutical formulations of the invention further comprise a glidant. In an embodiment, the glidant is fumed silica, alternatively referred to as colloidal silicon dioxide. In an embodiment, the colloidal silicon dioxide is present in an amount from about 0.1% w/w to about 0.5% w/w. In an embodiment, the colloidal silicon dioxide is present in an amount of about 0.25% w/w. In an embodiment, the colloidal silicon dioxide is present in an amount of about 0.26% w/w. In an embodiment, the colloidal silicon dioxide is present in an amount of 0.25% w/w. In an embodiment, the colloidal silicon dioxide is present in an amount of 0.26% w/w.

In another embodiment, the pharmaceutical formulations of the invention further comprise a lubricant. In an embodiment, the lubricant is stearic acid. In an embodiment, the stearic acid is present in an amount from about 1% w/w to about 3% w/w. In an embodiment, the stearic acid is present in an amount of about 2% w/w.

In another embodiment, the pharmaceutical formulations of the invention further comprise a filler. In an embodiment, the filler is microcrystalline cellulose. In an embodiment, the microcrystalline cellulose is present in an amount that makes the remaining percentage of the tablet relative to the rest of the components, including tenapanor.

In another embodiment of the pharmaceutical formulations of the invention, tenapanor drug substance (API or active pharmaceutical ingredient) has a particle diameter distribution D50 of about 18 μm to about 22 μm. In an embodiment, the particle diameter distribution D50 is from about 19 μm to about 21 μm. In an embodiment, the particle diameter distribution D50 is about 19 μm. In an embodiment, the particle diameter distribution D50 is about 20 μm. In an embodiment, the particle diameter distribution D50 is about 21 μm.

In another embodiment, the pharmaceutical formulation of the invention is in tablet form. In an embodiment, the tablet comprises an immediate release film-coating. In an embodiment, the immediate release film-coating comprises polyvinyl acetate.

In an embodiment, the amount of tenapanor in the tablet is about 10 mg. In an embodiment, the amount of tenapanor in the tablet is about 20 mg. In an embodiment, the amount of tenapanor in the tablet is about 30 mg. In an embodiment, the amount of tenapanor in the tablet is about 40 mg. In an embodiment, the amount of tenapanor in the tablet is about 50 mg. In an embodiment, the amount of tenapanor in the tablet is about 60 mg. In an embodiment, the amount of tenapanor in the tablet r is about 70 mg. In an embodiment, the amount of tenapanor in the tablet is about 80 mg. In an embodiment, the amount of tenapanor in the tablet is about 90 mg. In an embodiment, the amount of tenapanor in the tablet is about 100 mg.

In a particular embodiment, the pharmaceutical formulation of the invention comprises 10% w/w of amorphous tenapanor bis-HCl, 1.0% w/w tartaric acid and 0.2% w/w propyl gallate. In another embodiment, the pharmaceutical formulation further comprises 5.0% w/w of low-substituted hydroxypropyl cellulose. In another embodiment, the pharmaceutical formulation further comprises 0.26% w/w of colloidal silicon dioxide. In another embodiment, the pharmaceutical formulation further comprises 2.0% w/w of stearic acid. In another embodiment, the pharmaceutical formulation further comprises 80.5% w/w of microcrystalline cellulose.

In another particular embodiment, the pharmaceutical formulation comprises about 10 mg of tenapanor hydrochloride, about 0.2 mg of propyl gallate, about 1.0 mg of tartaric acid, about 1.2 mg of stearic acid, about 3.0 mg of low-substituted hydroxypropyl cellulose, about 0.26 mg of colloidal silicon dioxide and about 81 mg of microcrystalline cellulose.

In another particular embodiment, the pharmaceutical formulation comprises 10.64 mg of tenapanor hydrochloride, 0.20 mg of propyl gallate, 1.00 mg of tartaric acid, 1.20 mg of stearic acid, 3.00 mg of low-substituted hydroxypropyl cellulose, 0.26 mg of colloidal silicon dioxide and 80.96 mg of microcrystalline cellulose.

In another particular embodiment, the pharmaceutical formulation comprises about 20 mg of tenapanor hydrochloride, about 0.4 mg of propyl gallate, about 2.0 mg of tartaric acid, about 2.4 mg of stearic acid, about 6.0 mg of low-substituted hydroxypropyl cellulose, about 0.52 mg of colloidal silicon dioxide and about 162 mg of microcrystalline cellulose.

In another particular embodiment, the pharmaceutical formulation comprises 21.28 mg of tenapanor hydrochloride, 0.40 mg of propyl gallate, 2.00 mg of tartaric acid, 2.40 mg of stearic acid, 6.00 mg of low-substituted hydroxypropyl cellulose, 0.52 mg of colloidal silicon dioxide and 161.92 mg of microcrystalline cellulose.

In another particular embodiment, the pharmaceutical formulation comprises about 30 mg of tenapanor hydrochloride, about 0.6 mg of propyl gallate, about 3.0 mg of tartaric acid, about 3.6 mg of stearic acid, about 9.0 mg of low-substituted hydroxypropyl cellulose, about 0.78 mg of colloidal silicon dioxide and about 243 mg of microcrystalline cellulose.

In another particular embodiment, the pharmaceutical formulation comprises 31.92 mg of tenapanor hydrochloride, 0.60 mg of propyl gallate, 3.00 mg of tartaric acid, 3.60 mg of stearic acid, 9.00 mg of low-substituted hydroxypropyl cellulose, 0.78 mg of colloidal silicon dioxide and 242.88 mg of microcrystalline cellulose.

In another particular embodiment, the pharmaceutical formulation comprises about 50 mg of tenapanor hydrochloride, about 1.0 mg of propyl gallate, about 5.0 mg of tartaric acid, about 10.0 mg of stearic acid, about 25 mg of low-substituted hydroxypropyl cellulose, about 1.3 mg of colloidal silicon dioxide and about 405 mg of microcrystalline cellulose.

In another particular embodiment, the pharmaceutical formulation comprises 53.2 mg of tenapanor hydrochloride, 1.0 mg of propyl gallate, 5.0 mg of tartaric acid, 10.0 mg of stearic acid, 25.0 mg of low-substituted hydroxypropyl cellulose, 1.3 mg of colloidal silicon dioxide and 404.8 mg of microcrystalline cellulose.

EXAMPLES

Example 1 Synthesis of Tenapanor FB and Tenapanor HCl

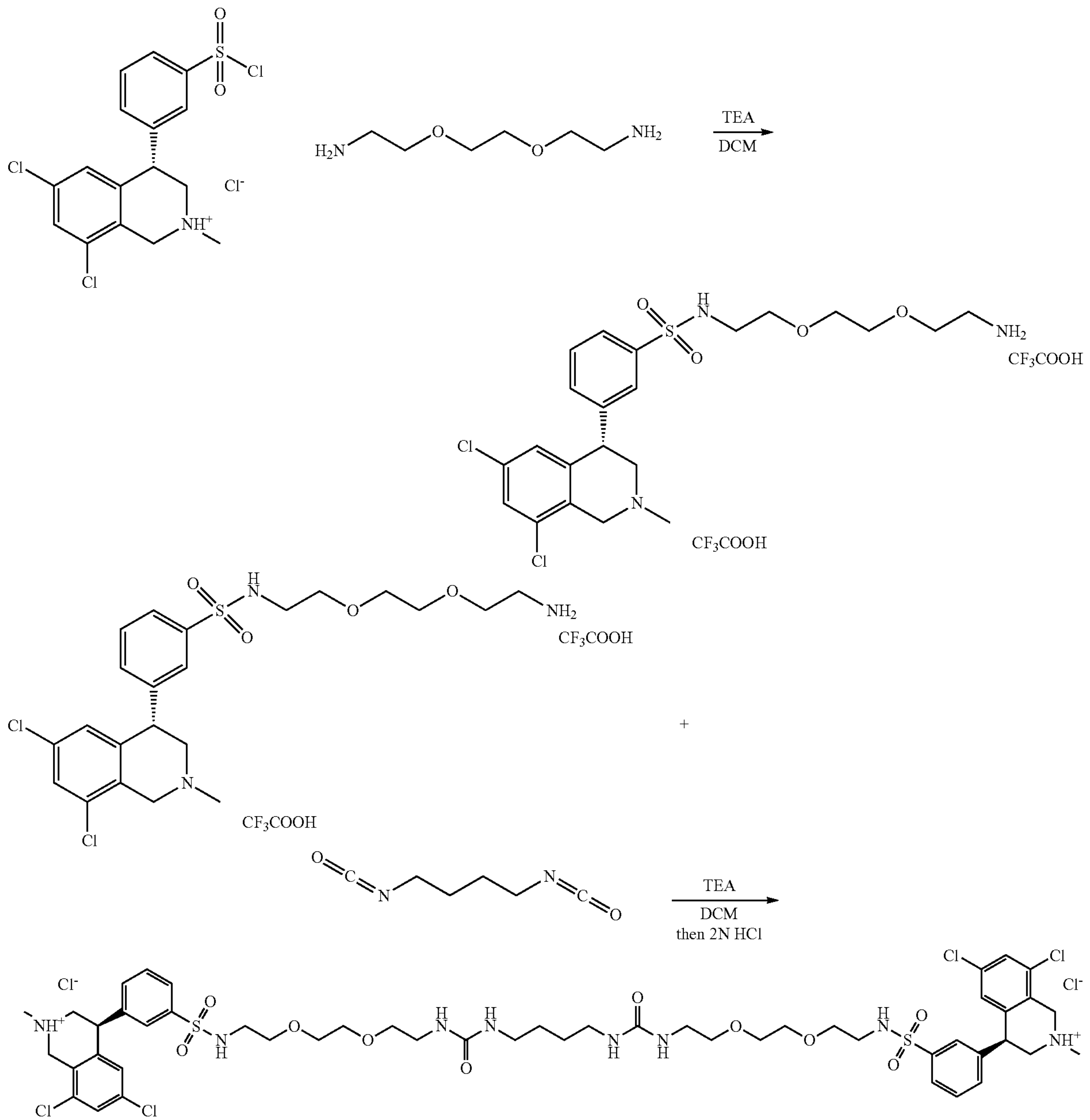

To 2-(2-(2-aminoethoxy) ethoxy) ethanamine (30.4 g, 205.41 mmol, 8.01 equiv) in dichloromethane (1000 mL) was added triethylamine (5.2 g, 51.49 mmol, 2.01 equiv). This was followed by the addition of(S)-3-(6,8-dichloro-2-methyl-1,2,3,4-tetrahydroisoquinolin-4-yl)benzene-1-sulfonyl chloride hydrochloride (10 g, 23.42 mmol, 1.00 equiv; prepared from intermediate 244.1 and the procedures described in Example 1) in portions at 10° C. in 1 h. The resulting solution was stirred for 15 min at room temperature. The resulting mixture was washed with 3×500 mL of brine, dried over anhydrous sodium sulfate and concentrated under vacuum. The residue was purified by Flash-Prep-HPLC with the following conditions: Column, C18 silica gel; mobile phase, methanol/water/TFA (4/100/0.0005) increasing to 8/10/0.0005 within 30 min; Detector, UV 254 nm. This resulted in 7.2 g (42%) of intermediate (S or R)—N-(2-(2-(2-aminoethoxy) ethoxy)ethyl)-3-(6,8-dichloro-2-methyl-1,2,3,4-tetrahydroisoquinolin-4-yl)benzenesulfonamide bis(2,2,2-trifluoroacetate) as a white solid.

To the intermediate above (500 mg, 0.69 mmol, 1.00 equiv) in DCM (10 mL) was added triethylamine (138 mg, 1.37 mmol, 1.99 equiv) followed by the addition of 1,4-diisocyanatobutane (48 mg, 0.34 mmol, 0.50 equiv) in portions. The resulting solution was stirred for 10 min at room temperature then the crude tenapanor free-base product (500 mg) was purified by Flash-Prep-HPLC with the following conditions: Column, C18 silica gel; mobile phase, methanol/water=0.05/100 increasing to 90/100 within 30 min; Detector, UV 254 nm.

To the tenapanor free-base product was added 0.2 mL of hydrochloric acid (2 N) and the solution lyophilized to afford 246.7 mg (59%) of amorphous tenapanor bis-HCl as a white solid. 1H-NMR (400 MHZ, CD3OD, ppm): 7.92 (d, J=7.2 Hz, 2H), 7.83 (s, 2H), 7.69-7.65 (m, 2H), 7.60-7.55 (m, 4H), 6.81 (s, 2H), 4.87-4.83 (m, 4H), 4.54-4.50 (m, 2H), 3.94-3.91 (m, 2H), 3.69-3.49 (m, 18H), 3.39-3.32 (m, 4H), 3.21-3.15 (m, 10H), 3.08-3.05 (m, 4H), 1.57 (s, 4H). LCMS (ES, m/z): 1145 [M−2HCl+1]+.

Example 2 Preparing Amorphous Tenapanor Bis-HCl by Spray Drying Tenapanor Free Base Crude tenapanor free base is dissolved in a solution of methanol/water, then tenapanor free base seed crystals are added to induce crystallization. The resulting slurry is cooled, and the product is collected by filtration, washed with methanol/water, and then dried to afford tenapanor free base, pure. To an agitated mixture of crystalline tenapanor free base, pure, in methanol is added concentrated hydrochloride acid until the pH is ≤0.6. The solution is spray dried, with particle size assessed by laser diffraction and spray drying parameters adjusted as needed to ensure the particle size distribution d(v,50)≤20 μm and d(v,90): 20-40 μm. The resulting powders are secondarily dried to achieve methanol content ≤3,000 ppm to afford tenapanor hydrochloride.

Example 3 Dissolution Experiments of Tablets N1-N28

The dissolution was performed using a USP 2 dissolution apparatus (paddle) at 75 rpm and 37° C. The dissolution medium (500 mL) used was citrate buffer pH4, ionic strength 0.1M. Samples were collected at relevant time points and the amount dissolved was then analyzed on a reversed-phase liquid chromatographic gradient system and quantified by its UV response at 210 nm against a fully characterized reference standard.

The invention claimed is:

1. A pharmaceutical formulation comprising, greater than 6% w/w of amorphous tenapanor bis-HCl as an active ingredient, propyl gallate, tartaric acid, hydroxypropyl cellulose, and stearic acid, wherein the total chloride content of said active ingredient is greater than 5.82%.

* * * * *